United States Patent
Zhang et al.

(10) Patent No.: US 8,211,148 B2
(45) Date of Patent: Jul. 3, 2012

(54) PROSTHESES FOR LOCKING AN ARTIFICIAL DISC IN AN INTERVERTEBRAL DISC SPACE

(75) Inventors: Jeffrey Zhang, Collierville, TN (US); Randy N. Allard, Germantown, TN (US)

(73) Assignee: Warsaw Orthopedic, Warsaw, IN (US)

( * ) Notice: Subject to any disclaimer, the term of this patent is extended or adjusted under 35 U.S.C. 154(b) by 426 days.

(21) Appl. No.: 11/789,272

(22) Filed: Apr. 24, 2007

(65) Prior Publication Data
US 2008/0269806 A1 Oct. 30, 2008

(51) Int. Cl.
*A61B 17/70* (2006.01)
(52) U.S. Cl. .................................................... 606/257
(58) Field of Classification Search .... 623/17.11–17.16; 606/257
See application file for complete search history.

(56) References Cited

U.S. PATENT DOCUMENTS

| | | | |
|---|---|---|---|
| 5,676,701 A * | 10/1997 | Yuan et al. | 623/17.15 |
| 6,231,610 B1 | 5/2001 | Geisler | |
| 6,461,359 B1 | 10/2002 | Tribus et al. | |
| 6,579,290 B1 * | 6/2003 | Hardcastle et al. | 606/247 |
| 6,682,563 B2 | 1/2004 | Scharf | |
| 6,730,127 B2 | 5/2004 | Michelson | |
| 6,740,088 B1 * | 5/2004 | Kozak et al. | 606/286 |
| 6,740,118 B2 * | 5/2004 | Eisermann et al. | 623/17.14 |
| 6,837,905 B1 | 1/2005 | Lieberman | |
| 6,884,242 B2 | 4/2005 | LeHuec et al. | |
| 6,899,735 B2 * | 5/2005 | Coates et al. | 623/17.16 |
| 6,984,234 B2 | 1/2006 | Bray | |
| 2004/0092929 A1 * | 5/2004 | Zindrick | 606/61 |
| 2007/0021837 A1 * | 1/2007 | Ashman | 623/17.16 |

* cited by examiner

*Primary Examiner* — Thomas C. Barrett
*Assistant Examiner* — Sameh Boles (57) ABSTRACT

A surgical implant for locking a spinal motion segment includes an anterior plate portion with laterally spaced interbody members extending posteriorly therefrom. The plate portion has passages to receive surgical fixing screws or other securing elements engaged in holes drilled in the vertebrae for securing the plate portion to the anterior faces of the vertebrae to be locked. The arms extend into a space between lateral portions of the vertebrae to be locked.

46 Claims, 4 Drawing Sheets

PROSTHESES FOR LOCKING AN ARTIFICIAL DISC IN AN INTERVERTEBRAL DISC SPACE

BACKGROUND

The present application relates to the field of spinal implants and, in particular, anterior vertebral implant locking devices and methods and systems for immobilizing a spinal motion segment by engaging an anterior vertebral implant locking device to same.

The spinal column of vertebrates provides support to bear weight and protection to the delicate spinal cord and spinal nerves. The spinal column comprises a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, the laminar arch, which covers the neural structures of the spinal cord and nerves for protection. Each vertebral body has relatively strong bone comprising the outside surface of the body (cortical) and relatively weak bone comprising the center of the body (cancellous). Between each vertebral body is an intervertebral disc, a cartilaginous cushion to help absorb impact and dampen compressive forces on the spine. At the junction of the arch and anterior vertebral body are articulations to allow movement of the spine.

Various types of problems can affect the structure and function of the spinal column. These can be based on degenerative conditions of the intervertebral disc or the articulating joints, traumatic disruption of the disc, bone or ligaments supporting the spine, tumor or infection. In addition, congenital or acquired deformities can cause abnormal angulation or slippage of the spine. Slippage (spondylolisthesis) of one vertebral body on another can cause compression of the spinal cord or nerves. Patients who suffer from one of more of these conditions often experience extreme and debilitating pain, and can sustain permanent neurologic damage if the conditions are not treated appropriately.

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are indicated to insure the proper spacing of the vertebrae formerly separated by the removed disc tissue.

In some instances, the two adjacent vertebrae are fused together using transplanted bone tissue, an artificial fusion component, or other compositions or devices. One potential side effect of spinal fusion procedures that has raised concerns in the medical community is that the bio-mechanical rigidity of intervertebral fusion may predispose neighboring spinal motion segments to rapid deterioration. More specifically, unlike a natural intervertebral disc, spinal fusion prevents the fused vertebrae from pivoting and rotating with respect to one another. Such lack of mobility tends to increase stresses on adjacent spinal motion segments. Additionally, several conditions may develop within adjacent spinal motion segments, including disc degeneration, disc herniation, instability, spinal stenosis, spondylosis and facet joint arthritis. Consequently, many patients may require additional disc removal and/or another type of surgical procedure as a result of spinal fusion.

An alternative to spinal fusion that has been given much attention is the use of intervertebral disc arthroplaty devices, such as articulating artificial disc devices. Several different types of intervertebral disc arthroplasty devices have been proposed for preventing the collapse of the intervertebral space between adjacent vertebrae while maintaining a certain degree of stability and range of pivotal and rotational motion therebetween. Such devices typically include two or more articular elements that are attached to respective upper and lower vertebrae. The articular elements can be anchored to the upper and lower vertebrae by a variety of methods, including the use of bone screws that pass through corresponding openings in each of the elements and thread into vertebral bone, and/or by the inclusion of spikes or teeth that penetrate the vertebral endplates to inhibit migration or expulsion of the device. The articular elements are typically configured to allow the elements, and correspondingly the adjacent vertebrae, to pivot and/or rotate relative to one another.

For a variety of reasons, it is sometimes necessary to take remedial measures as a result of a failure of an artificial disc devices or to immobilize a motion segment for other reasons. For example, it is possible that an artificial disc could become displaced from its intended position, possibly resulting in or resulting from damage or weakening of surrounding bone. Moreover, in the case of articulating discs, it is possible that the articulating interfaces could become inoperable due to wear or due to the presence of foreign objects that interfere with its operation. Remedial measures can include, for example, replacement of an artificial disc with a new disc arthroplaty device or fusion of the motion segment.

There is a continuing need for advancements in the relevant field, including new devices, systems and methods for remedying a failed artificial disc and devices, systems and methods for immobilizing a spinal motion segment for other reasons. The present application addresses this need and provides a variety of additional benefits and advantages.

SUMMARY

The present application involves surgical implants for locking spinal motion segments. A device provided by the present application includes an anterior plate portion with laterally spaced interbody members extending posteriorly therefrom. The plate portion has passages to receive surgical fixing screws or other securing elements engaged in holes drilled in the vertebrae for securing the plate portion to the anterior faces of the vertebrae to be locked. The arms extend into a space between lateral portions of the vertebrae to be locked.

In one aspect, the present application provides a method for locking a spinal motion segment that includes an artificial disc positioned in an interbody space between first and second vertebrae. The method includes: (1) providing a disc locking implant device that includes first and second spaced apart lateral interbody wing members each having an anterior end and a posterior end, and an anterior retention plate affixed to the anterior end of each of said wing members; (2) positioning the disc locking implant device in an orientation whereby the first and second wing members reside in the interbody space between lateral portions of the first and second vertebrae, the anterior retention plate is adjacent anterior surfaces of the first and second vertebrae, and at least a portion of the artificial disc lies between said first and second interbody wing members; and (3) securing the anterior retention plate to the first and second vertebrae to hold the first and second wing members and first and second vertebrae in a locked orientation relative to one another.

In another aspect of the application, there is provided a system for locking a spinal motion segment. The system includes: (1) an artificial disc secured to first and second adjacent vertebrae of a spinal motion segment in an interbody space between said first and second vertebrae; and (2) a disc locking implant device secured to the first and second vertebrae, the disc locking implant device including first and second spaced apart lateral interbody wing members each having an anterior end and a posterior end, and an anterior retention plate affixed to the anterior end of each of said wing members, the plate being configured for attachment to the first and second vertebrae to hold first and second wing members and first and second vertebrae in a locked orientation relative to one another.

In yet another aspect, the application provides a disc locking implant device. In one embodiment, the device includes first and second spaced apart lateral interbody wing members each having an anterior end and a posterior end; and an anterior retention plate affixed to the anterior end of each of the wing members, the plate being configured for attachment to the first and second vertebrae to hold the first and second wing members and the first and second vertebrae in a locked orientation relative to one another. In this embodiment, each of the first and second interbody members is adapted for insertion into an interbody disc space between the first and second vertebrae to laterally embrace an artificial disc device positioned in the interbody space.

In another embodiment, a disc locking implant device includes first and second spaced apart lateral interbody wing members adapted for insertion into an interbody disc space between lateral portions of adjacent first and second vertebrae to laterally embrace an artificial disc device positioned in the interbody disc space; and means for fixing the first and second interbody wing members in lateral interbody locking positions.

In yet another embodiment, a spinal disc locking implant device includes first and second spaced apart lateral interbody wing members each having an anterior end and a posterior end; and an anterior retention plate affixed to the anterior end of each of the wing members. The plate is configured for placement at a location spanning the first and second adjacent vertebrae on an anterior side of the first and second vertebrae. The plate has an anterior side, a posterior side, and a plurality of apertures passing through the plate and adapted to receive a respective one of a plurality of securing elements for securing the plate to the first and second vertebrae to hold first and second wing members and first and second vertebrae in a locked orientation relative to one another. In this embodiment, each of the securing element receiving apertures is positioned at an offset location on a first side of a midline of the first and second vertebrae.

Further embodiments, forms, features and aspects of the present application shall become apparent from the detailed description and figures provided herewith.

DETAILED DESCRIPTION OF SELECTED EMBODIMENTS

For the purposes of promoting an understanding of the principles of the inventions described herein, reference will now be made to the embodiments illustrated in the drawings and specific language will be used to describe the same. It will nevertheless be understood that no limitation of the scope of any subject matter described and claimed herein is thereby intended. Any alterations and further modifications in the illustrated embodiments, and any further applications of the principles described and illustrated herein, are contemplated as would normally occur to one skilled in the art.

Spinal disc locking implant devices provided by the present application find excellent use in an operation where, for whatever reason, it is necessary or desirable to lock a disc in the interbody disc space without revision, i.e., to remedy a failed artificial disc device in an interbody disc space between a pair of adjacent vertebrae without removing the artificial disc device from the interbody disc space. For example, the locking implant devices can be used to lock a spinal motion segment that includes an artificial articulating disc as described in U.S. Pat. No. 6,740,118 to Eisermann et al., which is hereby incorporated herein in its entirety. In such an operation, the disc is left in place and first and second lateral wing members are inserted into an interbody location between opposing lateral portions of the adjacent vertebrae from the anterior side of the spinal column, with one interbody member placed on one lateral side of the artificial disc and the other interbody member placed on the opposite lateral side of the artificial disc. In addition, a fixation plate is rigidly connected to the lateral wing members to hold the lateral wing members in place, and is also affixed to each of the adjacent vertebrae using fixation screws or other fixation devices. As will be appreciated by a person skilled in the relevant field, the spinal disc locking implant devices provided herein can also be used to advantage to lock spinal motion segments that include a natural disc rather than an artificial disc. The terms "locking" and "lock," as used herein in connection with a spinal disc locking implant device, are intended to mean that the spinal disc locking implant device is operable to constrain the motions of the motion segment.

Figure 1:
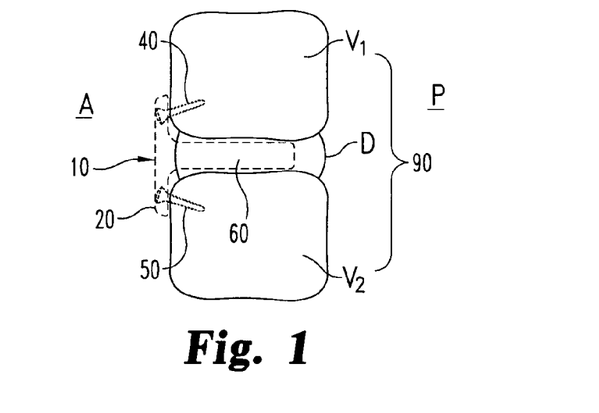
FIG. 1 is a diagrammatic side elevation view of a spinal column motion segment including vertebrae $V_1$ and $V_2$ and artificial disc D, with an embodiment of a locking device in accordance with the present application shown in phantom in an implanted position.
Figure 2:
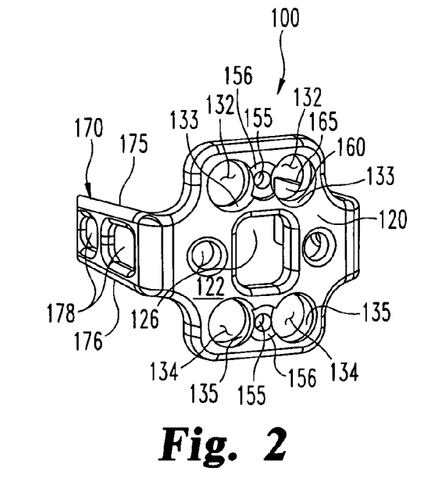
FIG. 2 is a perspective view of another embodiment of a locking device in accordance with the present application.
Figure 3:
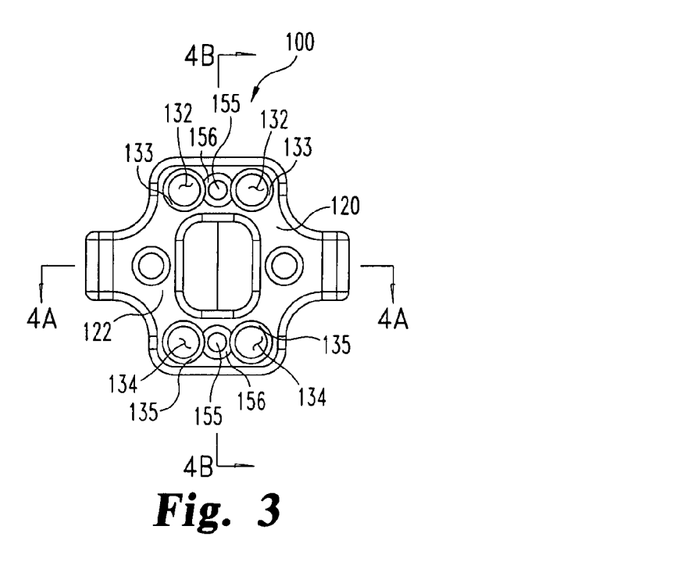
FIG. 3 is a front elevation view of the embodiment depicted in FIG. 2.
Figure 4A:
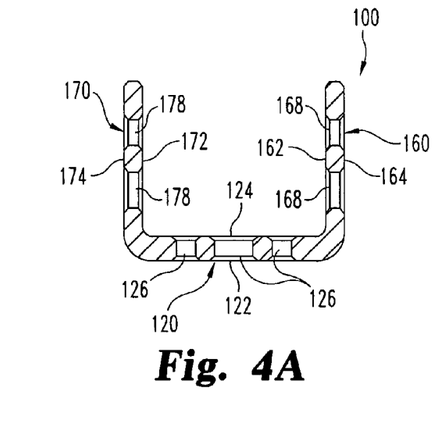
FIG. 4A is a cross sectional view of the embodiment depicted in FIGS. 2 and 3 along the line 4A-4A shown in FIG. 3.
Figure 4B:
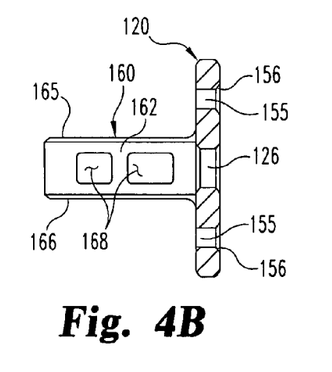
FIG. 4B is a cross sectional view of the embodiment depicted in FIGS. 2 and 3 along the line 4B-4B shown in FIG. 3.

A diagrammatic side view of motion segment 90 is depicted in FIG. 1, in which a first vertebral body $V_1$ and adjacent vertebral body $V_2$ have disc D positioned therebetween. Disc D can be an artificial disc or a natural disc in alternative embodiments. Vertebral body $V_1$ (also referred to herein as "vertebra $V_1$") is in a superior position with regard to vertebral body $V_2$ (also referred to herein as "vertebra $V_2$"), which is correspondingly in an inferior position with regard to vertebral body $V_1$. In FIG. 1, the letter "A" is used to identify the anterior side of vertebrae $V_1$, $V_2$, and the letter "P" is used to identify the posterior side of vertebrae $V_1$, $V_2$. Spinal disc locking implant device 10 is shown in phantom as it would be positioned after implant, namely, with retention plate 20 positioned anteriorly to portions of vertebrae $V_1$, $V_2$ and spanning the interbody space in which disc D is positioned. Lateral interbody wing members are represented in FIG. 1 by reference numeral 60 to show generally the positioning of wing members 60 from a lateral perspective after the device is implanted. Retention plate 20 is affixed to vertebra $V_1$ using one or more superior side fixation screws 40 and is affixed to vertebra $V_2$ using one or more inferior side fixation screws 50. With device 10 implanted as shown in FIG. 1, with wing members positioned in the interbody disc space between vertebrae $V_1$, $V_2$ and with fixation screws 40, 50 securely fastening retention plate 20 to vertebrae $V_1$, $V_2$, motion segment 90 is locked. The lateral wing members 60 operate to constrain flexion, extension and lateral bending of motion segment 90, and fixation screws 40, 50 operate to constrain rotation of motion segment 90.

With reference to the embodiment depicted in FIGS. 2-5, spinal disc locking implant device 100 includes a symmetrical retention plate configured for receiving dual screws placed symmetrically in each of the superior and inferior portions of the plate. Device 100 includes retention plate 120 sized and configured for placement at a location anterior to portions of first vertebra $V_1$ and adjacent second vertebra $V_2$, and spanning the interbody space between vertebrae $V_1$ and $V_2$, as shown most clearly in FIG. 5. Plate 120 has an anterior side 122, a posterior side 124, two apertures 132 through plate 120 in a superior portion of plate 120 that are adapted to receive fixation screws 140 for securing plate 120 to vertebra $V_1$, and two apertures 134 through plate 120 in an inferior portion of plate 120 that are adapted to receive fixation screws 150 for securing plate 120 to vertebra $V_2$. If desired, plate 120 can have a profiled posterior surface 124 for engagement with corresponding anterior faces of vertebrae $V_1$ and $V_2$ when the device is in the implanted position. In this regard, plate 120 can have a flat profile, a curved profile, or can have other contours to facilitate its attachment to vertebrae $V_1$ and $V_2$.

Apertures 134, 136 are sized and configured to allow passage of a shaft of bone screw 140, 150 therethrough and to retain a head portion of bone screw 140, 150. In the embodiment shown, apertures 134, 136 have tapered portions 133, 135 for engaging head portions of screws 140, 150. In other embodiments (not shown) apertures 132, 134 can have other geometries than those shown, and different types of screws, bone anchors or other fixation devices can be employed in place of screws 140, 150. For example, apertures 132, 134 can have a generally conical shape to receive a bone screw having a radiused head. As used herein, the term "radiused head" means that the lower portion of the bone screw head, i.e., the portion that is nearest the shank, is generally rounded, to thereby permit the bone screw to toggle within its hole or slot. A wide variety of alternative fixation devices are known to persons of ordinary skill in the art and available commercially. Bone screws 140, 150 can be made of any suitable material, and in certain embodiments are made of the same material as the base plate 120, such as, for example, titanium or a titanium alloy. Moreover, the bone screws 140, 150 can all have the same shape or can have different shapes.

Plate 120 also includes openings 155 for receiving locking screws 157. The term "locking" as used in connection with locking screws 157 refers to the ability of locking screws 157 to prevent bone screws 140, 150 from backing out from the bone once screwed in through retention plate 120 (i.e., to "lock" the bone screws in place). The present application also contemplates that alternative configurations can alternatively be employed in place of locking screws 157 to achieve this bone screw locking function. For example, a locking plate and locking plate fixing means can be used in alternative embodiments, examples of which are known in the art. In the embodiment shown in FIGS. 2-5, openings 155 include tapered portions 156 for receiving a bottom surface of screw 157 of corresponding dimensions. Plate 120 also includes optional openings 126.

Attached to plate 120 are first and second spaced apart lateral interbody wing members, 160 and 170, respectively, that extend generally perpendicularly from plate 120 in a direction toward the posterior side P of vertebrae $V_1$, $V_2$. Each of members 160, 170 is adapted for insertion into an interbody space between first and second vertebrae $V_1$ and $V_2$ to laterally embrace an artificial disc device positioned in the interbody space. Each of interbody wing members 160, 170 includes a respective inner surface 162, 172, a respective outer surface 164, 174, a respective top edge 165, 175 and a respective bottom edge 166, 176. In addition, in the embodiment depicted in FIGS. 2-5, wing members 160, 170 include optional openings 168, 178.

In one embodiment, inner surfaces 162, 172 of wing members 160, 170 are spaced and configured to engage lateral contours of an artificial disc D positioned in the interbody disc space between vertebrae $V_1$, $V_2$. For example, with reference again to U.S. Pat. No. 6,740,118 to Eisermann et al., channels 57, 107 are formed in lateral edges of articulating implant embodiments shown and described therein (see, e.g., FIG. 20 of Eiserman et al.). Inner surfaces 162, 172 of wing members 160, 170 can be formed to have corresponding contours (not shown) such that insertion of wing members 160, 170 into the interbody space causes the contours of inner surfaces 162, 172 to engage channels of the Eisermann et al. embodiments. It is, of course, to be understood that artificial discs can have a wide variety of different lateral contours, and the present application is not intended to be limited to any specific shape or size thereof.

In one embodiment, top edge 165 and bottom edge 166 of wing member 160 are parallel to one another and top edge 175 and bottom edge 176 of wing member 170 are parallel to one another. In another embodiment, top edge 165 and bottom edge 166 of wing member 160 form an angle with one another and top edge 175 and bottom edge 176 of wing member 170 form a similar angle with one another. For example, the respective top edges 165, 175 can be angled with respect to bottom edges 166, 176, respectively, such that wing members 160, 170 have a tapered profile in the anterior to posterior direction. Such an embodiment can be employed to restore or correct the lordotic sagittal balance of a patient's spine. It is to be understood that a wide variety of angles can be employed, and a preferred angle for a given operation will depend on a variety of factors, including, for example, the specific anatomic features of a given patient and the specific goals of the operation. In alternative embodiments, wing members 160, 170 feature different profiles, i.e., top edge 165 and bottom edge 166 of wing member 160 form an angle that is different than an angle formed by top edge 175 and bottom edge 176 of wing member 170, or where one but not the other of wing members 160, 170 is parallel.

In yet another embodiment, wing members 160, 170 are formed such that top edges 165, 175 and bottom edges 166, 176, which are bone-contacting surfaces of wing members 160, 170, are shaped to reduce the tendency of edges 165, 175, 166, 176 to subside or sink into the endplates of vertebrae $V_1$ and $V_2$. For example, wing members 160, 170 can be formed such that each of edges 165, 175, 166, 176 is relatively wider in a lateral direction than another portion of wing members 160, 170. In other embodiments, only one, two or three of edges 165, 175, 166, 176 is shaped to reduce its tendency to subside in an endplate as described above.

A patient in need of treatment to lock a spinal motion segment in accordance with the teachings of the present application is prepped appropriately for anterior spine surgery using techniques well known in the relevant field. The surgeon then uses standard anterior surgical approaches to isolate two or more vertebral bodies to be treated. A curette or similar surgical instrument can be used to prepare the vertebral bodies and plates for receiving the anterior fixation device. The surgeon then selects an appropriate disc locking implant device having proper dimensions and features for the particular motion segment, and inserts the device between the adjacent vertebral bodies such that the lateral wing members extend into the interbody space in a direction between anterior and posterior. For example, device 100 is fixed in place by inserting wing members 160, 170 into proper lateral positions in the interbody space such that edges 165, 175 engage a lateral portion of the inferior surface of the body of vertebra $V_1$ and edges 166, 176 engage a lateral portion of the superior surface of the body of vertebra $V_2$, and such that surface 124 of plate 120 contacts an anterior surface of both vertebrae $V_1$ and $V_2$.

Once the wing members are properly placed between adjacent vertebral bodies, the surgeon next secures the device to the adjacent vertebrae by inserting at least two bone screws or other securing elements through the bone screw apertures and into the vertebral bodies. To insert the bone screws, holes are first formed in vertebrae $V_1$, $V_2$ in proper position and orientation to receive screws or other bone anchors through apertures 132, 134. Holes can be formed, for example, using drills or other bone cutting tools and using apertures 132, 134 in retention plate 120 as guides. As is generally known in the art, a drilling tool may be used to drill holes in the bone to "tap" or prep the bone for receiving the bone screws 140, 150. If desired before drilling, a tack tool, a tool having an elongated stem and a removable sharp tack at its distal end, may be used to create a starter hole in the bone to facilitate drilling. After drilling, a tapping tool may be used to tap the drilled holes. Following tapping, the bone screws 140, 150 are screwed into the drilled and tapped holes through the apertures 132, 134 of plate 120.

In one embodiment, apertures 132, 134 in retention plate 120 are formed to receive screws 140, 150 or other anchors at an angle other than 90 degrees (also referred to as an "inclination"), relative to plate 120 and to the anterior surfaces of vertebrae $V_1$ and $V_2$. In one embodiment, bone screws 140, 150 are introduced into the first and second vertebrae $V_1$, $V_2$ so that the axis of each bone screw is at an angle relative to the bone surface ranging from about 20° to about 70°. In another embodiment, the angle is from about 40° to about 60°. While it is not intended that the present application be limited by any theory, it is believed that such an inclination may enhance the stability of implant device 100 when fixed in place, more effectively preventing implant device 100 from working loose than if the apertures 132, 134 were mutually parallel or parallel to the direction of wing members 160, 170. After holes are formed in appropriate places, screws 140, 150 or other bone anchors are inserted through each aperture 132, 134 in retention plate 120 and into the respective holes in vertebrae $V_1$, $V_2$. Each screw 140, 150 is tightened until the head of the screw is seated against the tapered surface 133, 135, at which point the vertebrae $V_1$, $V_2$ are securely fixed to device 100 and securely fixed relative to each other, with wing members positioned as desired.

After screws 140, 150 are in a tightened position, threaded locking screws 157 are inserted into respective correspondingly threaded openings 155 in plate 120 and tightened until the head of each screw is seated against the tapered surface 156, at which point screws 140, 150 or other bone anchors positioned in apertures 132, 134 are locked in place to prevent back-out of screws 140, 150 or other bone anchors. Once the spinal column has been appropriately treated, the surgeon then finishes the anterior surgery using well-known surgical techniques.

In the above-described procedure, it is generally intended for the implant device 100 to remain permanently in place; however, there may be circumstances in which it is necessary or desirable for it to be removed. Should this be necessary, the implant can be withdrawn by unscrewing the bone screws 140, 150 and withdrawing the implant. The generally U-shaped arrangement of wing members 160, 170 and plate 120 (from a top view) allows for device 100 to be readily slidable into position over a disc already present in the disc space without removing the disc, and for device 100 to be readily slidable away from the spinal column to withdraw wing members 160, 170 from the interbody space and to remove the implant, if desired. Thus, replacement or permanent removal of the implant can be achieved without causing significant trauma to the adjacent vertebrae, interbody tissues or surrounding tissues.

When spinal disc locking device 100 is intended to remain permanently in place, the device can be used together with bone growth facilitating materials or other bioactive agents to promote fusion of the adjacent vertebrae $V_1$, $V_2$. Thus, an operation to implant device 100 for permanent residence can also include, after positioning device 100 in a desired location and orientation relative to vertebrae $V_1$, $V_2$ and disc D, a bone growth facilitating material is positioned in one or more spaces defined by wing members 160, 170, plate 120, disc D and vertebrae $V_1$, $V_2$. One or more bone growth facilitating materials can be introduced and packed into such spaces, for example, through one or more of openings 126, 168, 178, if present. In an alternative embodiment, plate 120 may not include an opening. In embodiments having no opening, the spaces can be packed with a bone growth facilitating material prior to placement of the device as described herein. Examples of bone growth facilitating materials that can be employed include, for example, bone fragments, bone growth factors, such as, for example, bone morphogenic protein, or other materials promoting the growth of bone, blood vessels or other tissue. It is not intended, however, that the present application be limited to the identified materials, it being understood that a wide variety of alternative materials can be selected and used together with or as substitutes for the materials named.

Figures 5, 6, 7:
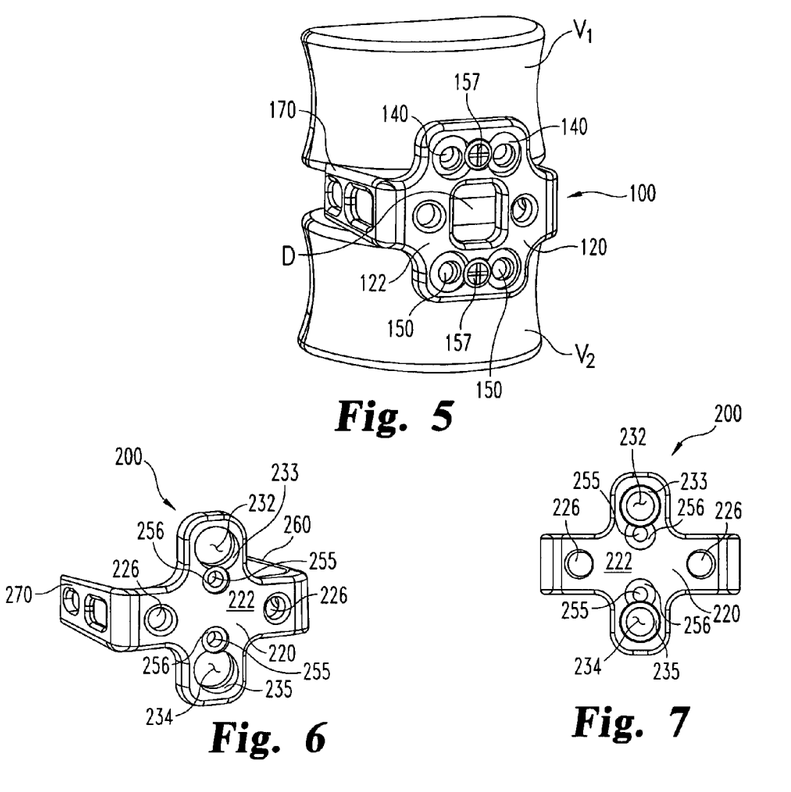
FIG. 5 is a perspective view of the embodiment depicted in FIGS. 2-4B diagrammatically shown in its orientation relative to vertebrae $V_1$ and $V_2$ after implant.
FIG. 6 is a perspective view of another embodiment of a locking device in accordance with the present application.
FIG. 7 is a front elevation view of the embodiment depicted in FIG. 6.
Figure 8:
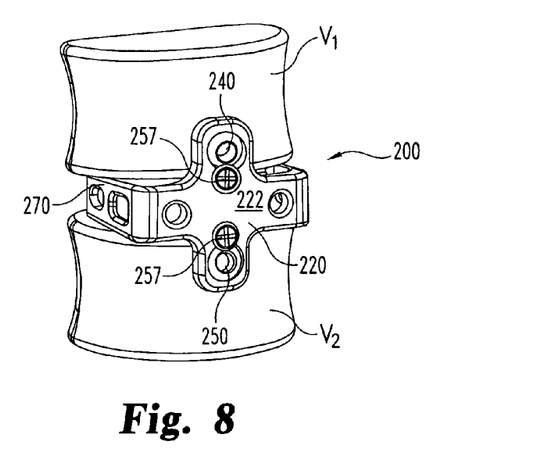
FIG. 8 is a perspective view of the embodiment depicted in FIGS. 6 and 7 diagrammatically shown in its orientation relative to vertebrae $V_1$ and $V_2$ after implant.

With reference now to the embodiment depicted in FIGS. 6-8, spinal disc locking implant device 200 includes a retention plate configured for receiving a single screw placed symmetrically in each of the superior and inferior portions of the plate. Retention plate 220 is sized and configured for placement at a location anterior to portions of first vertebra $V_1$ and adjacent second vertebra $V_2$, and spanning the interbody space between vertebrae $V_1$ and $V_2$, as shown most clearly in FIG. 8. Plate 220 has an anterior side 222, a posterior side (not shown), an aperture 232 through plate 220 in a superior portion of plate 220 that is adapted to receive a fixation screw 240 for securing plate 220 to vertebra $V_1$, and an aperture 234 through plate 220 in an inferior portion of plate 220 that is adapted to receive fixation screw 250 for securing plate 220 to vertebra $V_2$. If desired, plate 220 can have a profiled posterior surface for engagement with corresponding anterior faces of vertebrae $V_1$ and $V_2$ when the device is in the implanted position. In this regard, plate 220 can have a flat profile, a curved profile, or can have other contours to facilitate its attachment to vertebrae $V_1$ and $V_2$.

Apertures 234, 236 are sized and configured to allow passage of a shaft of bone screw 240, 250 therethrough and to retain a head portion of bone screw 240, 250. In the embodiment shown, apertures 234, 236 have tapered portions 233, 235 for engaging head portions of screws 240, 250. In other embodiments (not shown) apertures 232, 234 can have other geometries than those shown, and different types of screws, bone anchors or other fixation devices can be employed in place of screws 240, 250. A wide variety of such alternative fixation devices are known to persons of ordinary skill in the art and available commercially. Bone screws 240, 250 can be made of any suitable material, and in certain embodiments are made of the same material as the base plate 220, such as, for example, titanium or a titanium alloy.

Plate 220 also includes openings 255 for receiving locking screws 257. The present application also contemplates that alternative configurations can be employed in place of locking screws 257 to achieve the bone screw locking function. For example, a locking plate and locking plate fixing means can be used in alternative embodiments, examples of which are known in the art and available commercially. In the embodiment shown in FIGS. 6-8, openings 255 include tapered portions 256 for receiving a bottom surface of screw 257 of corresponding dimensions. Plate 220 also includes optional openings 226.

Attached to plate 220 are first and second spaced apart lateral interbody wing members, 260 and 270, respectively, that extend generally perpendicularly from plate 220 in a direction toward the posterior side P of vertebrae $V_1$, $V_2$. Each of members 260, 270 is adapted for insertion into an interbody space between first and second vertebrae $V_1$ and $V_2$ to laterally embrace an artificial disc device positioned in the interbody space. Each of interbody wing members 260, 270 includes a respective inner surface similar to inner surfaces 162, 172 described in connection with device 100, a respective outer surface similar to outer surfaces 164, 174 described in connection with device 100, a respective top edge similar to top edges 165, 175 described in connection with device 100 and a respective bottom edge similar to bottom edges 166, 176 described in connection with device 100. In addition, in the embodiment depicted in FIGS. 6-8, wing members 260, 270 include optional openings similar to optional openings 168, 178 described in connection with device 100.

In one embodiment, the inner surfaces of wing members 260, 270 are spaced and configured to engage lateral contours of an artificial disc D positioned in the interbody disc space between vertebrae $V_1$, $V_2$ as described above in connection with device 100. The inner surfaces of wing members 260, 270 can be formed to have corresponding contours (not shown) such that insertion of wing members 260, 270 into the interbody space causes the contours of the inner surfaces to engage corresponding lateral contours of an artificial disc residing in the interbody disc space. It is, of course, to be understood that artificial discs can have a wide variety of different lateral contours, and the present application is not intended to be limited to any specific shape or size thereof. In addition, the top and bottom edges of wing members 260, 270 can be formed to be parallel to one another or to form an angle with respect to one another as described above in connection with top edges 165, 175 and bottom edges 166, 176 of wing members 160, 170. Also, one or both of wing members 260, 270 can be formed such that one or more of the top edges or bottom edges thereof are shaped to reduce the tendency of the edges to subside or sink into the endplates of vertebrae $V_1$ and $V_2$ as described above in connection with wing members 160, 170.

Device 200 is fixed in place by inserting wing members 260, 270 into proper lateral positions in the interbody space such that the respective top edges thereof engage respective lateral portions of the inferior surface of the body of vertebra $V_1$ and the respective bottom edges thereof engage respective lateral portions of the superior surface of the body of vertebra $V_2$, and such that the posterior surface of plate 220 contacts an anterior surface of both vertebrae $V_1$ and $V_2$. Once device 200 has been positioned, holes are formed in vertebrae $V_1$, $V_2$ in proper position and orientation to receive screws or other bone anchors through apertures 232, 234. Holes can be formed, for example, using drills or other bone cutting tools and using apertures 232, 234 in retention plate 220 as guides. In one embodiment, apertures 232, 234 in retention plate 220 can be formed to receive screws 240, 250 or other anchors at an inclination, or angle other than 90 degrees, relative to plate 220. After holes are formed in appropriate places, screws 240, 250 or other bone anchors are inserted through each aperture 232, 234 in retention plate 220 and into the respective holes in vertebrae $V_1$, $V_2$. Each screw 240, 250 is tightened until the head of the screw is seated against the tapered surface 233, 235, at which point the vertebrae $V_1$, $V_2$ are securely fixed to device 200 and securely fixed relative to each other, with wing members positioned as desired.

After screws 240, 250 are in a tightened position, threaded locking screws 257 are inserted into respective correspondingly threaded openings 255 in plate 220 and tightened until the head of each screw is seated against the tapered surface 256, at which point screws 240, 250 or other bone anchors positioned in apertures 232, 234 are locked in place to prevent back-out of screws 240, 250 or other bone anchors. In alternative embodiments, a bone screw retaining means other than a locking screw can be employed, it being understood that a wide variety of means for securely covering at least a part of each of the bone screws 240, 250 will be effective to prevent the bone screws from backing out from the bone once screwed in through plate 220. For example, in another embodiment, the bone screw locking means can include a locking plate (not shown) and a locking plate fixing means.

Device 200 can be implanted with the intent of allowing it to remain permanently in place; however, it can be removed if desired in a manner similar to that described above in connection with device 100. In addition, as described above in connection with device 100, when spinal disc locking device 200 is intended to remain permanently in place, the device can be used together with bone growth facilitating materials or other bioactive agents to promote fusion of the adjacent vertebrae $V_1$, $V_2$.

Figure 9:
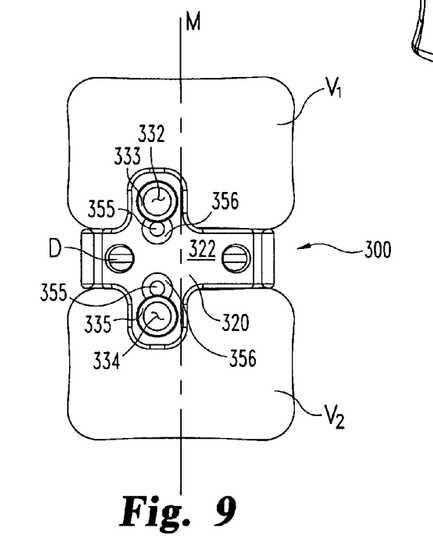
FIG. 9 is a front elevation view of another embodiment of a locking device in accordance with the present application diagrammatically shown in its orientation to vertebrae $V_1$ and $V_2$ after implant.
Figure 10:
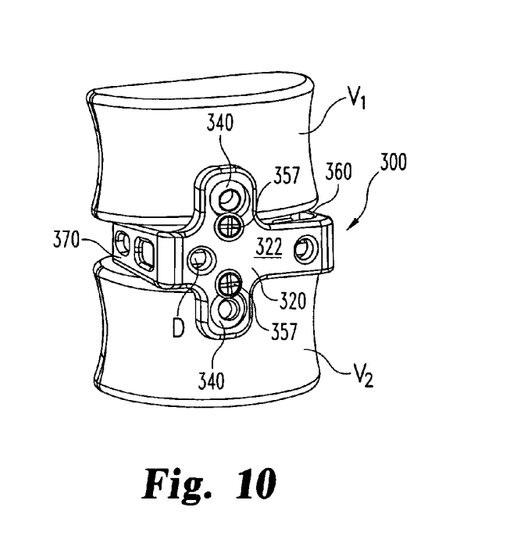
FIG. 10 is a perspective view of the embodiment depicted in FIG. 9 diagrammatically shown in its orientation relative to vertebrae $V_1$ and $V_2$ after implant.

With reference now to the embodiment depicted in FIGS. 9-10, spinal disc locking implant device 300 includes an offset, non-symmetrical retention plate configured for receiving a single screw placed in each of the superior and inferior portions of the plate. The superior portion and inferior portions defining apertures for receiving the screws are offset to the same side of a midline M defined by vertebrae $V_1$, $V_2$. Device 300 includes retention plate 320 sized and configured for placement at a location anterior to portions of first vertebra $V_1$ and adjacent second vertebra $V_2$, and spanning the interbody space between vertebrae $V_1$ and $V_2$, as shown most clearly in FIG. 10. Plate 320 has an anterior side 322, a posterior side (not shown), an aperture 332 through plate 320 in a superior portion of plate 320 that is adapted to receive a fixation screw 340 for securing plate 320 to vertebra $V_1$, and an aperture 334 through plate 320 in an inferior portion of plate 320 that is adapted to receive fixation screw 350 for securing plate 320 to vertebra $V_2$. If desired, plate 320 can have a profiled posterior surface for engagement with corresponding anterior faces of vertebrae $V_1$ and $V_2$ when the device is in the implanted position. In this regard, plate 320 can have a flat profile, a curved profile, or can have other contours to facilitate its attachment to vertebrae $V_1$ and $V_2$.

Apertures 334, 336 are sized and configured to allow passage of a shaft of bone screw 340, 350 therethrough and to retain a head portion of bone screw 340, 350. In the embodiment shown, apertures 334, 336 have tapered portions 333, 335 for engaging head portions of screws 340, 350. In other embodiments (not shown) apertures 332, 334 can have other geometries than those shown, and different types of screws, bone anchors or other fixation devices can be employed in place of screws 340, 350. A wide variety of such alternative fixation devices are known to persons of ordinary skill in the art and available commercially. Bone screws 340, 350 can be made of any suitable material, and in certain embodiments are made of the same material as the base plate 320, such as, for example, titanium or a titanium alloy.

Plate 320 also includes openings 355 for receiving locking screws 357. The present application also contemplates that alternative configurations can be employed in place of locking screws 357 to achieve the bone screw locking function. For example, a locking plate and locking plate fixing means can be used in alternative embodiments, examples of which are known in the art and available commercially. In the embodiment shown in FIGS. 9-10, openings 355 include tapered portions 356 for receiving a bottom surface of screw 357 of corresponding dimensions. Plate 320 also includes optional openings 326.

Attached to plate 320 are first and second spaced apart lateral interbody wing members, 360 and 370, respectively, that extend generally perpendicularly from plate 320 in a direction toward the posterior side P of vertebrae $V_1$, $V_2$. Each of members 360, 370 is adapted for insertion into an interbody space between first and second vertebrae $V_1$ and $V_2$ to laterally embrace an artificial disc device positioned in the interbody space. Each of interbody wing members 360, 370 includes a respective inner surface similar to inner surfaces 162, 172 described in connection with device 100, a respective outer surface similar to outer surfaces 164, 174 described in connection with device 100, a respective top edge similar to top edges 165, 175 described in connection with device 100 and a respective bottom edge similar to bottom edges 166, 176 described in connection with device 100. In addition, in the embodiment depicted in FIGS. 9-10, wing members 360, 370 include optional openings similar to optional openings 168, 178 described in connection with device 100.

In one embodiment, the inner surfaces of wing members 360, 370 are spaced and configured to engage lateral contours of an artificial disc D positioned in the interbody disc space between vertebrae $V_1$, $V_2$ as described above in connection with device 100. The inner surfaces of wing members 360, 370 can be formed to have corresponding contours (not shown) such that insertion of wing members 360, 370 into the interbody space causes the contours of the inner surfaces to engage lateral contours of an artificial disc residing in the interbody disc space. It is, of course, to be understood that artificial discs can have a wide variety of different lateral contours, and the present application is not intended to be limited to any specific shape or size thereof. In addition, the top and bottom edges of wing members 360, 370 can be formed to be parallel to one another or to form an angle with respect to one another as described above in connection with top edges 165, 175 and bottom edges 166, 176 of wing members 160, 170. Also, one or both of wing members 360, 370 can be formed such that one or more of the top edges or bottom edges thereof are shaped to reduce the tendency of the edges to subside or sink into the endplates of vertebrae $V_1$ and $V_2$ as described above in connection with wing members 160, 170.

Device 300 is fixed in place by inserting wing members 360, 370 into proper lateral positions in the interbody space such that the respective top edges thereof engage respective lateral portions of the inferior surface of the body of vertebra $V_1$ and the respective bottom edges thereof engage respective lateral portions of the superior surface of the body of vertebra $V_2$, and such that the posterior surface of plate 320 contacts an anterior surface of both vertebrae $V_1$ and $V_2$. Once device 300 has been positioned, holes are formed in vertebrae $V_1$, $V_2$ in proper position and orientation to receive screws or other bone anchors through apertures 332, 334. Holes can be formed, for example, using drills or other bone cutting tools and using apertures 332, 334 in retention plate 320 as guides. In one embodiment, apertures 332, 334 in retention plate 320 can be formed to receive screws 340, 350 or other anchors at an inclination, or angle other than 90 degrees, relative to plate 320. After holes are formed in appropriate places, screws 340, 350 or other bone anchors are inserted through each aperture 332, 334 in retention plate 320 and into the respective holes in vertebrae $V_1$, $V_2$. Each screw 340, 350 is tightened until the head of the screw is seated against the tapered surface 333, 335, at which point the vertebrae $V_1$, $V_2$ are securely fixed to device 300 and securely fixed relative to each other, with wing members positioned as desired.

After screws 340, 350 are in a tightened position, threaded locking screws 357 are inserted into respective correspondingly threaded openings 355 in plate 320 and tightened until the head of each screw is seated against the tapered surface 356, at which point screws 340, 350 or other bone anchors positioned in apertures 332, 334 are locked in place to prevent back-out of screws 340, 350 or other bone anchors.

Device 300 can be implanted with the intent of allowing it to remain permanently in place; however, it can be removed at a later time, if desired, in a manner similar to that described above in connection with devices 100 and 200. In addition, as described above in connection with devices 100 and 200, when spinal disc locking device 300 is intended to remain permanently in place, the device can be used together with bone growth facilitating materials or other bioactive agents to promote fusion of the adjacent vertebrae $V_1$, $V_2$.

Figure 11:
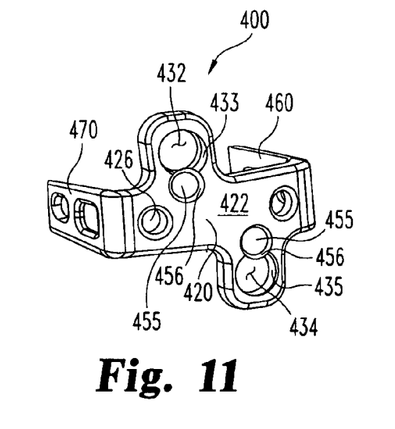
FIG. 11 is a perspective view of another embodiment of a locking device in accordance with the present application.
Figure 12:
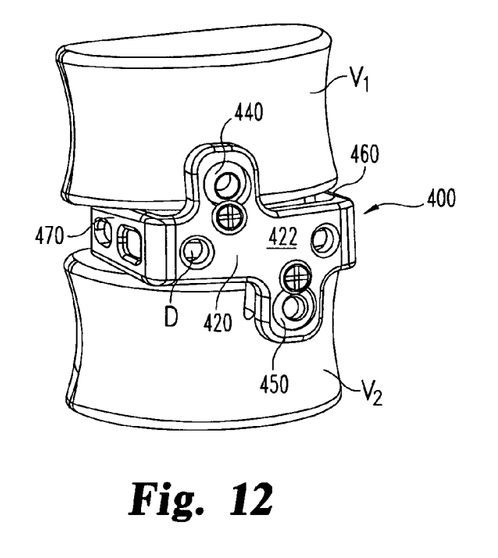
FIG. 12 is a perspective view of the embodiment depicted in FIG. 11 diagrammatically shown in its orientation relative to vertebrae $V_1$ and $V_2$ after implant.

With reference now to the embodiment depicted in FIGS. 11-12, spinal disc locking implant device 400 includes a symmetrical retention plate configured for receiving a single screw placed in each of the superior and inferior portions of the plate in a diagonal orientation. The superior portion defining an aperture for receiving a screw is offset to one side of a midline M defined by vertebrae $V_1$, $V_2$, and the inferior portion defining an aperture for receiving a screw is offset to the opposite side of the midline M. Device 400 includes retention plate 420 sized and configured for placement at a location anterior to portions of first vertebra $V_1$ and adjacent second vertebra $V_2$, and spanning the interbody space between vertebrae $V_1$ and $V_2$, as shown most clearly in FIG. 12. Plate 420 has an anterior side 422, a posterior side (not shown), an aperture 432 through plate 420 in a superior portion of plate 420 that is adapted to receive a fixation screw 440 for securing plate 420 to vertebra $V_1$, and an aperture 434 through plate 420 in an inferior portion of plate 420 that is adapted to receive fixation screw 450 for securing plate 420 to vertebra $V_2$. If desired, plate 420 can have a profiled posterior surface for engagement with corresponding anterior faces of vertebrae $V_1$ and $V_2$ when the device is in the implanted position. In this regard, plate 420 can have a flat profile, a curved profile, or can have other contours to facilitate its attachment to vertebrae $V_1$ and $V_2$ Apertures 434, 436 are sized and configured to allow passage of a shaft of bone screw 440, 450 therethrough and to retain a head portion of bone screw 440, 450. In the embodiment shown, apertures 434, 436 have tapered portions 433, 435 for engaging head portions of screws 440, 450. In other embodiments (not shown) apertures 432, 434 can have other geometries than those shown, and different types of screws, bone anchors or other fixation devices can be employed in place of screws 440, 450. A wide variety of such alternative fixation devices are known to persons of ordinary skill in the art and available commercially. Bone screws 440, 450 can be made of any suitable material, and in certain embodiments are made of the same material as the base plate 420, such as, for example, titanium or a titanium alloy.

Plate 420 also includes openings 455 for receiving locking screws 457. The present application also contemplates that alternative configurations can be employed in place of locking screws 457 to achieve the bone screw locking function. For example, a locking plate and locking plate fixing means can be used in alternative embodiments, examples of which are known in the art and available commercially. In the embodiment shown in FIGS. 9-10, openings 455 include tapered portions 456 for receiving a bottom surface of screw 457 of corresponding dimensions. Plate 420 also includes optional openings 426.

Attached to plate 420 are first and second spaced apart lateral interbody wing members, 460 and 470, respectively, that extend generally perpendicularly from plate 420 in a direction toward the posterior side P of vertebrae $V_1$, $V_2$ Each of members 460, 470 is adapted for insertion into an interbody space between first and second vertebrae $V_1$ and $V_2$ to laterally embrace an artificial disc device positioned in the interbody space. Each of interbody wing members 460, 470 includes a respective inner surface similar to inner surfaces 162, 172 described in connection with device 100, a respective outer surface similar to outer surfaces 164, 174 described in connection with device 100, a respective top edge similar to top edges 165, 175 described in connection with device 100 and a respective bottom edge similar to bottom edges 166, 176 described in connection with device 100. In addition, in the embodiment depicted in FIGS. 9-10, wing members 460, 470 include optional openings similar to optional openings 168, 178 described in connection with device 100.

In one embodiment, the inner surfaces of wing members 460, 470 are spaced and configured to engage lateral contours of an artificial disc D positioned in the interbody disc space between vertebrae $V_1$, $V_2$ as described above in connection with device 100. The inner surfaces of wing members 460, 470 can be formed to have corresponding contours (not shown) such that insertion of wing members 460, 470 into the interbody space causes the contours of the inner surfaces to engage lateral contours of an artificial disc residing in the interbody disc space. It is, of course, to be understood that artificial discs can have a wide variety of different lateral contours, and the present application is not intended to be limited to any specific shape or size thereof. In addition, the top and bottom edges of wing members 460, 470 can be formed to be parallel to one another or to form an angle with respect to one another as described above in connection with top edges 165, 175 and bottom edges 166, 176 of wing members 160, 170. Also, one or both of wing members 460, 470 can be formed such that one or more of the top edges or bottom edges thereof are shaped to reduce the tendency of the edges to subside or sink into the endplates of vertebrae $V_1$ and $V_2$ as described above in connection with wing members 160, 170.

Device 400 is fixed in place by inserting wing members 460, 470 into proper lateral positions in the interbody space such that the respective top edges thereof engage respective lateral portions of the inferior surface of the body of vertebra $V_1$ and the respective bottom edges thereof engage respective lateral portions of the superior surface of the body of vertebra $V_2$, and such that the posterior surface of plate 420 contacts an anterior surface of both vertebrae $V_1$ and $V_2$. Once device 400 has been positioned, holes are formed in vertebrae $V_1$, $V_2$ in proper position and orientation to receive screws or other bone anchors through apertures 432, 434. Holes can be formed, for example, using drills or other bone cutting tools and using apertures 432, 434 in retention plate 420 as guides. In one embodiment, apertures 432, 434 in retention plate 420 can be formed to receive screws 440, 450 or other anchors at an inclination, or angle other than 90 degrees, relative to plate 420. After holes are formed in appropriate places, screws 440, 450 or other bone anchors are inserted through each aperture 432, 434 in retention plate 420 and into the respective holes in vertebrae $V_1$, $V_2$. Each screw 440, 450 is tightened until the head of the screw is seated against the tapered surface 433, 435, at which point the vertebrae $V_1$, $V_2$ are securely fixed to device 400 and securely fixed relative to each other, with wing members positioned as desired.

After screws 440, 450 are in a tightened position, threaded locking screws 457 are inserted into respective correspondingly threaded openings 455 in plate 420 and tightened until the head of each screw is seated against the tapered surface 456, at which point screws 440, 450 or other bone anchors positioned in apertures 432, 434 are locked in place to prevent back-out of screws 440, 450 or other bone anchors.

Device 400 can be implanted with the intent of allowing it to remain permanently in place; however, it can be removed if desired in a manner similar to that described above in connection with devices 100, 200 and 300. In addition, as described above in connection with devices 100, 200 and 300, when spinal disc locking device 400 is intended to remain permanently in place, the device can be used together with bone growth facilitating materials or other bioactive agents to promote fusion of the adjacent vertebrae $V_1$, $V_2$.

Figure 13:
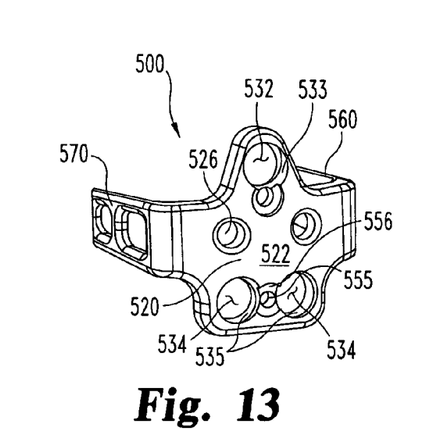
FIG. 13 is a perspective view of another embodiment of a locking device in accordance with the present application.
Figure 14:
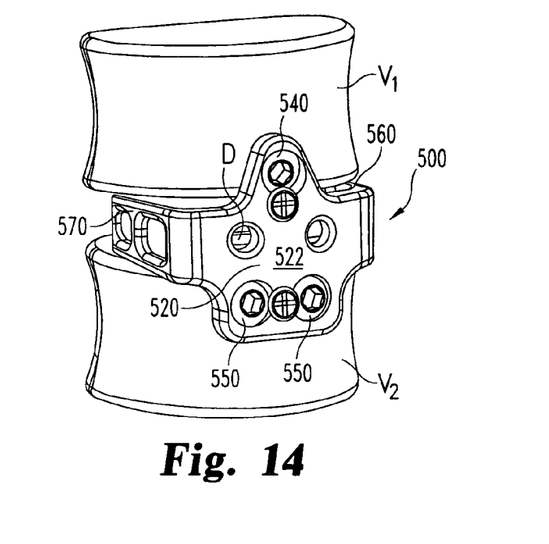
FIG. 14 is a perspective view of the embodiment depicted in FIG. 13 diagrammatically shown in its orientation relative to vertebrae $V_1$ and $V_2$ after implant.

With reference now to the embodiment depicted in FIGS. 13-14, spinal disc locking implant device 500 includes a central triangular symmetrical retention plate configured for receiving a single screw placed in the superior portion of the plate and dual screws placed in the inferior portion of the plate. Device 500 includes retention plate 520 sized and configured for placement at a location anterior to portions of first vertebra V₁ and adjacent second vertebra V₂, and spanning the interbody space between vertebrae V₁ and V₂, as shown most clearly in FIG. 12. Plate 520 has an anterior side 522, a posterior side (not shown), an aperture 532 through plate 520 in a superior portion of plate 520 that is adapted to receive a fixation screw 540 for securing plate 520 to vertebra V₁, and an aperture 534 through plate 520 in an inferior portion of plate 520 that is adapted to receive fixation screw 550 for securing plate 520 to vertebra V₂. If desired, plate 520 can have a profiled posterior surface for engagement with corresponding anterior faces of vertebrae V₁ and V₂ when the device is in the implanted position. In this regard, plate 520 can have a flat profile, a curved profile, or can have other contours to facilitate its attachment to vertebrae V₁ and V₂.

Apertures 534, 536 are sized and configured to allow passage of a shaft of bone screw 540, 550 therethrough and to retain a head portion of bone screw 540, 550. In the embodiment shown, apertures 534, 536 have tapered portions 533, 535 for engaging head portions of screws 540, 550. In other embodiments (not shown) apertures 532, 534 can have other geometries than those shown, and different types of screws, bone anchors or other fixation devices can be employed in place of screws 540, 550. A wide variety of such alternative fixation devices are known to persons of ordinary skill in the art and available commercially. Bone screws 540, 550 can be made of any suitable material, and in certain embodiments are made of the same material as the base plate 520, such as, for example, titanium or a titanium alloy.

Plate 520 also includes openings 555 for receiving locking screws 557. The present application also contemplates that alternative configurations can be employed in place of locking screws 557 to achieve the bone screw locking function. For example, a locking plate and locking plate fixing means can be used in alternative embodiments, examples of which are known in the art and available commercially. In the embodiment shown in FIGS. 9-10, openings 555 include tapered portions 556 for receiving a bottom surface of screw 557 of corresponding dimensions. Plate 520 also includes optional openings 526.

Attached to plate 520 are first and second spaced apart lateral interbody wing members, 560 and 570, respectively, that extend generally perpendicularly from plate 520 in a direction toward the posterior side P of vertebrae V₁, V₂. Each of members 560, 570 is adapted for insertion into an interbody space between first and second vertebrae V₁ and V₂ to laterally embrace an artificial disc device positioned in the interbody space. Each of interbody wing members 560, 570 includes a respective inner surface similar to inner surfaces 162, 172 described in connection with device 100, a respective outer surface similar to outer surfaces 164, 174 described in connection with device 100, a respective top edge similar to top edges 165, 175 described in connection with device 100 and a respective bottom edge similar to bottom edges 166, 176 described in connection with device 100. In addition, in the embodiment depicted in FIGS. 9-10, wing members 560, 570 include optional openings similar to optional openings 168, 178 described in connection with device 100.

In one embodiment, the inner surfaces of wing members 560, 570 are spaced and configured to engage lateral contours of an artificial disc D positioned in the interbody disc space between vertebrae V₁, V₂ as described above in connection with device 100. The inner surfaces of wing members 560, 570 can be formed to have corresponding contours (not shown) such that insertion of wing members 560, 570 into the interbody space causes the contours of the inner surfaces to engage lateral contours of an artificial disc residing in the interbody disc space. It is, of course, to be understood that artificial discs can have a wide variety of different lateral contours, and the present application is not intended to be limited to any specific shape or size thereof. In addition, the top and bottom edges of wing members 560, 570 can be formed to be parallel to one another or to form an angle with respect to one another as described above in connection with top edges 165, 175 and bottom edges 166, 176 of wing members 160, 170. Also, one or both of wing members 560, 570 can be formed such that one or more of the top edges or bottom edges thereof are shaped to reduce the tendency of the edges to subside or sink into the endplates of vertebrae V₁ and V₂ as described above in connection with wing members 160, 170.

Device 500 is fixed in place by inserting wing members 560, 570 into proper lateral positions in the interbody space such that the respective top edges thereof engage respective lateral portions of the inferior surface of the body of vertebra V₁ and the respective bottom edges thereof engage respective lateral portions of the superior surface of the body of vertebra V₂, and such that the posterior surface of plate 520 contacts an anterior surface of both vertebrae V₁ and V₂. Once device 500 has been positioned, holes are formed in vertebrae V₁, V₂ in proper position and orientation to receive screws or other bone anchors through apertures 532, 534. Holes can be formed, for example, using drills or other bone cutting tools and using apertures 532, 534 in retention plate 520 as guides. In one embodiment, apertures 532, 534 in retention plate 520 can be formed to receive screws 540, 550 or other anchors at an inclination, or angle other than 90 degrees, relative to plate 520. After holes are formed in appropriate places, screws 540, 550 or other bone anchors are inserted through each aperture 532, 534 in retention plate 520 and into the respective holes in vertebrae V₁, V₂. Each screw 540, 550 is tightened until the head of the screw is seated against the tapered surface 533, 535, at which point the vertebrae V₁, V₂ are securely fixed to device 500 and securely fixed relative to each other, with wing members positioned as desired.

After screws 540, 550 are in a tightened position, threaded locking screws 557 are inserted into respective correspondingly threaded openings 555 in plate 520 and tightened until the head of each screw is seated against the tapered surface 556, at which point screws 540, 550 or other bone anchors positioned in apertures 532, 534 are locked in place to prevent back-out of screws 540, 550 or other bone anchors.

Device 500 can be implanted with the intent of allowing it to remain permanently in place; however, it can be removed if desired in a manner similar to that described above in connection with devices 100, 200, 300 and 400. In addition, as described above in connection with devices 100, 200, 300 and 400, when spinal disc locking device 500 is intended to remain permanently in place, the device can be used together with bone growth facilitating materials or other bioactive agents to promote fusion of the adjacent vertebrae V₁, V₂.

In one embodiment, the implant device 10, 100, 200, 300, 400, 500 is of unitary construction. In other embodiments, device 10, 100, 200, 300, 400, 500 includes multiple components that are connected together prior to or during an implantation operation. For example, device 10, 100, 200, 300, 400, 500 can include multiple parts welded or otherwise bonded together, joined by mechanical structures, such as screws or other fasteners or by other means. In one embodiment, some or all of implant device 10, 100, 200, 300, 400, 500 is made from a titanium alloy. It is to be understood, however, that this example is not meant to be limiting of the devices described and claimed herein, it being understood that a device in accordance with the present application can be made from a variety of alternative materials as would occur to a person of ordinary skill in the art.

In another aspect of the invention, a kit is provided that includes at least one disc locking implant device as described herein and at least two bone screws or other securing elements. In some embodiments, the kit also includes one or more locking screws or other locking means for attachment to the device to prevent back-out of bone screws or other securing element. In other embodiments, the kit also includes one or more of a tack tool, a drilling tool, a tapping tool and a screw driving tool. In yet another embodiment, the kit includes a plurality of separate and different disc locking implant devices. For example, in one embodiment, a kit includes disc locking implant devices of different sizes and/or shapes, bone screws of differing lengths and optionally one or more of a tack tool, a drilling tool, tapping tool and a screw driving tool.

While multiple embodiments have been illustrated and described in detail in the drawings and foregoing description, the same is to be considered illustrative and not restrictive in character, it being understood that only selected embodiments have been shown and described and that all changes, equivalents, and modifications as would occur to those skilled in the art and that come within the scope of the inventions described herein or defined by the following claims are desired to be protected. Any experiments, experimental examples, or experimental results provided herein are intended to be illustrative of the subject matter described and claimed in the present application and should not be construed to limit or restrict the scope of the application. Further, any theory, mechanism of operation, proof, or finding stated herein is meant to further enhance understanding of the present application and is not intended to limit the subject matter described and claimed herein in any way to such theory, mechanism of operation, proof, or finding. In addition, the various procedures, techniques, and operations may be altered, rearranged, substituted, deleted, duplicated, or combined as would occur to those skilled in the art. Further, any U.S. Patent, pending U.S. Patent Application Publication or other publication cited herein is incorporated herein by reference in its entirety as if each individual publication, patent, or patent application was specifically and individually indicated to be incorporated by reference and set forth in its entirety herein. In reading the claims, words such as the word "a," the word "an," the words "at least one," and the words "at least a portion" are not intended to limit the claims to only one item unless specifically stated to the contrary. Further, when the language "at least a portion" and/or "a portion" is used, the claims may include a portion and/or the entire item unless specifically stated to the contrary.

Any reference to a specific direction, for example, references to up, upper, down, lower, and the like, is to be understood for illustrative purposes only or to better identify or distinguish various components from one another. Any reference to a first or second vertebra or vertebral body is intended to distinguish between two vertebrae and is not intended to specifically identify the referenced vertebrae as adjacent vertebrae, the first and second cervical vertebrae or the first and second lumbar, thoracic, or sacral vertebrae. These references are not to be construed as limiting in any manner the medical devices and/or methods as described herein. Unless specifically identified to the contrary, all terms used herein are used to include their normal and customary terminology. Further, while various embodiments of medical devices having specific components and structures are described and illustrated herein, it is to be understood that any selected embodiment can include one or more of the specific components and/or structures described for another embodiment where possible.

What is claimed is:

1. A system for locking a spinal motion segment comprising:
   an artificial disc adapted to be secured to first and second adjacent vertebrae of a spinal motion segment in an interbody space between said first and second vertebrae; and
   a disc locking implant device adapted to be secured to the first and second vertebrae, the disc locking implant device including:
   first and second spaced apart lateral interbody wing members each having an anterior end and a posterior end; and
   an anterior retention plate affixed to the anterior end of each of said wing members, the plate being configured for attachment to the first and second vertebrae to hold said first and second wing members and the first and second vertebrae in a locked orientation relative to one another; and
   wherein said artificial disc comprises an articulating artificial disc at least partially positioned between said interbody wing members of said disc locking implant device, said articulating artificial disc configured to mimic the natural structure and function of a natural intervertebral disc to substantially preserve motion of the spinal motion segment without fusion between the first and second vertebrae, wherein said articulating artificial disc comprises at least two articular elements that articulate relative to one another prior to being at least partially positioned between said interbody wing members of said disc locking implant device, and wherein the anterior retention plate is configured to be positioned at a location and has a length adapted to span the first and second adjacent vertebrae on an anterior side of the first and second vertebrae.

2. The system in accordance with claim 1 wherein the disc locking implant device is configured to be positioned at a location whereby the first and second wing members reside in the interbody space between lateral portions of the first and second vertebrae, the anterior retention plate is adapted to be positioned adjacent anterior surfaces of the first and second vertebrae, and at least a portion of the artificial disc lies between said first and second interbody wing members.

3. The system in accordance with claim 1 wherein the plate has an anterior side, a posterior side, and a plurality of apertures passing through the plate and adapted to receive a respective one of a plurality of securing elements for securing the plate to the first and second vertebrae.

4. The system in accordance with claim 3 wherein each of said first and second wing members is affixed to and extends generally perpendicularly from the posterior side of the plate, said first and second wing members having inner surfaces that face toward one another and outer surfaces that face laterally away from one another.

5. The system in accordance with claim 3, further comprising:
   a first securing element positioned in said first aperture in a manner whereby the first securing element is adapted to be engaged to the first vertebra; and
   a second securing element positioned in said second aperture in a manner whereby the second securing element is adapted to be engaged to the second vertebra.

6. The system in accordance with claim 1 wherein said first and second wing members have first and second inner surfaces facing generally toward one another; and wherein said first and second lateral interbody wing members are positioned such that lateral contours defined by each of the inner surfaces engage corresponding lateral contours defined by first and second lateral surfaces of the artificial disc, respectively.

7. The system in accordance with claim 6 wherein said lateral contours defined by said first and second wing members comprise lateral projections; and wherein said corresponding lateral contours defined by said articulating artificial disc comprise lateral channels; and wherein said lateral projections are positioned within said lateral channels to thereby engage said articulating artificial disc to said disc locking implant device.

8. The system in accordance with claim 1 wherein each of the first and second lateral interbody wing members has a top edge and a bottom edge; and wherein the top and bottom edges of at least one of the first and second wing members are parallel.

9. The system in accordance with claim 1 wherein each of the first and second lateral interbody wing members has a top edge and a bottom edge; and wherein at least one edge selected from the group consisting of the top edge of the first wing member, the bottom edge of the first wing member, the top edge of the second wing member and the bottom edge of the second wing member is shaped to reduce subsidence of the edge into an endplate of the first or second vertebra.

10. The system in accordance with claim 1 wherein said disc locking implant device comprises:

a plate having an anterior side, a posterior side, and a plurality of apertures passing through the plate and adapted to receive a respective one of a plurality of securing elements for securing the plate to the first and second vertebrae;

a first securing element positioned in said first aperture and adapted to be engaged to the first vertebra;

a second securing element positioned in said second aperture and adapted to be engaged to the second vertebra; and first and second spaced apart interbody wing members, each of said members affixed to and extending generally perpendicularly from the posterior side of the plate, said first and second interbody wing members adapted for insertion between said first and second vertebrae and having inner surfaces facing generally toward one another;

wherein the locking implant device is oriented with respect to said disc in a manner whereby at least a portion of the artificial disc lies between said first and second interbody wing members; and wherein said disc and said locking implant are operable to lock the spinal motion segment.

11. The system in accordance with claim 1 wherein said plate comprises a profiled posterior surface configured to correspond to anterior faces of the first and second adjacent vertebrae.

12. The system in accordance with claim 1 wherein said articulating artificial disc is laterally embraced by said interbody wing members of said disc locking implant device when at least partially positioned therebetween.

13. The system in accordance with claim 12 wherein said first and second interbody wing members have respective inner surfaces facing generally toward one another; and wherein said inner surface of each of said first and second interbody wing members includes lateral contours that engage corresponding lateral contours of said articulating artificial disc to thereby engage said articulating artificial disc to said disc locking implant device.

14. The system in accordance with claim 13 wherein said lateral contours defined by said first and second interbody wing members comprise lateral projections; and wherein said corresponding lateral contours defined by said articulating artificial disc comprise lateral channels; and wherein said lateral projections are positioned within said lateral channels to thereby engage said articulating artificial disc to said disc locking implant device.

15. The system in accordance with claim 1 wherein said at least two articular elements rotate and pivot relative to one another prior to being at least partially positioned between said interbody wing members of said disc locking implant device.

16. The system in accordance with claim 1 wherein said at least two articular elements comprise:

a first articular element configured for engagement with the first vertebrae; and a second articular element configured for engagement with the second vertebrae.

17. The system in accordance with claim 16 wherein said first and second articular elements together define a joint that permits said first and second articular elements to rotate and pivot relative to one another prior to being at least partially positioned between said interbody wing members of said disc locking implant device.

18. The system in accordance with claim 1 wherein said retention plate has an anterior side, a posterior side, and lateral surfaces extending from said anterior side to said posterior side; and wherein each of said first and second wing members is affixed to and extends generally perpendicularly from said posterior side of said retention plate, said first and second wing members having inner surfaces that face toward one another and outer surfaces that face laterally away from one another and which extend from respective ones of said lateral surfaces of said retention plate to thereby provide said disc locking implant device with a U-shaped configuration.

19. The system in accordance with claim 1 wherein said anterior retention plate has a length adapted to span the interbody space between the first and second vertebrae;

wherein said anterior retention plate includes a first aperture passing through a superior portion of said plate positioned along a superior side of said artificial disc, said first aperture adapted to receive a first securing element for securing the plate to the first vertebrae; and wherein said anterior retention plate includes a second aperture passing through an inferior portion of said plate positioned along an inferior side of said artificial disc, said second aperture adapted to receive a second securing element for securing the plate to the second vertebrae.

20. A disc locking implant device comprising:

first and second spaced apart lateral interbody wing members each having an anterior end and a posterior end; and an anterior retention plate affixed to the anterior end of each of said wing members, the plate being configured for attachment to first and second vertebrae to hold said first and second wing members and the first and second vertebrae in a locked orientation relative to one another;

wherein each of said first and second interbody wing members is adapted for insertion into an interbody disc space between said first and second vertebrae to laterally embrace an artificial disc device positioned in the interbody space; and an articulating artificial disc at least partially positioned between and laterally embraced by said first and second interbody wing members, wherein said articulating artificial disc is configured to mimic the natural structure and function of a natural intervertebral disc to substantially preserve motion of a spinal motion segment without fusion between the first and second vertebrae, wherein said articulating artificial disc comprises at least two articular elements that articulate relative to one another prior to being at least partially positioned between said interbody wing members, and wherein said plate is configured to be positioned at a location spanning the first and second adjacent vertebrae on an anterior side of the first and second vertebrae.

21. The device in accordance with claim 20 wherein the disc locking implant device is configured to be positioned at a location whereby the first and second wing members reside in the interbody space between lateral portions of the first and second vertebrae, the anterior retention plate is adjacent anterior surfaces of the first and second vertebrae, and at least a portion of the artificial disc lies between said first and second interbody wing members.

22. The device in accordance with claim 20 wherein the anterior retention plate is configured to be secured to the first and second vertebrae to lock the spinal motion segment.

23. The device in accordance with claim 20
wherein the plate has an anterior side, a posterior side, and a plurality of apertures passing through the plate and adapted to receive a respective one of a plurality of securing elements for securing the plate to the first and second vertebrae.

24. The device in accordance with claim 23, further comprising at least one opening for receiving a locking screw operable to prevent back-out of securing elements positioned in one or more of said plurality of apertures.

25. The device in accordance with claim 20 wherein each of said first and second spaced apart interbody wing members is affixed to and extends generally perpendicularly from the posteriorside of the plate, said first and second interbody wing members having inner surfaces that face generally toward one another.

26. The device in accordance with claim 20, further comprising:
a first securing element positioned in said first aperture in a manner whereby the first securing element is engaged to the first vertebra; and
a second securing element positioned in said second aperture in a manner whereby the second securing element is engaged to the second vertebra.

27. The device in accordance with claim 20 wherein said first and second lateral interbody wing members have first and second inner surfaces facing generally toward one another; and
wherein said first and second lateral interbody wing members are positioned such that the inner surfaces engage first and second lateral surfaces of the artificial disc, respectively.

28. The device in accordance with claim 20 wherein said disc locking implant device comprises:
a plate positioned at a location spanning the first and second adjacent vertebrae on an anterior side of the first and second vertebrae, the plate having an anterior side, a posterior side, and plurality of apertures passing through the plate and adapted to receive a respective one of a plurality of securing elements for securing the plate to the first and second vertebrae;
a first securing element positioned in said first aperture and engaged to the first vertebra;
a second securing element positioned in said second aperture and engaged to the second vertebra; and
first and second spaced apart interbody members, each of said members affixed to and extending generally perpendicularly from the posterior side of the plate, said first and second interbody wing members adapted for insertion between said first and second vertebrae and having inner surfaces facing toward one another;
wherein the locking implant device is oriented with respect to said disc in a manner whereby at least a portion of the artificial disc lies between said first and second interbody wing members; and
wherein said disc and said locking implant are operable to lock the spinal motion segment.

29. The device in accordance with claim 20 wherein said plate comprises a profiled posterior surface corresponding to anterior faces of the first and second adjacent vertebrae when said members are located between said first and second vertebrae.

30. The device in accordance with claim 20 wherein said first and second interbody wing members have respective inner surfaces facing generally toward one another; and
wherein the inner surface of each of said first and second interbody wing members includes lateral contours that engage corresponding lateral contours of the articulating artificial disc.

31. The device in accordance with claim 30 wherein said lateral contours defined by said first and second interbody wing members comprise lateral projections; and
wherein said corresponding lateral contours defined by said articulating artificial disc comprise lateral channels; and
wherein said lateral projections are positioned within said lateral channels to thereby engage said articulating artificial disc to said disc interbody wing members.

32. The device in accordance with claim 20, further comprising at least one window formed in the plate, the window operable to allow viewing of the artificial disc and to allow passage of a surgical instrument.

33. The device in accordance with claim 20, further comprising at least one window formed in the first and second interbody wing members, the window operable to allow viewing of the artificial disc and to allow passage of a surgical instrument.

34. The device in accordance with claim 20 wherein each of said interbody wing members has a height sufficiently large that said members engage the first and second vertebrae.

35. The device in accordance with claim 20 wherein each of the first and second lateral interbody wing members has a top edge and a bottom edge; and
wherein the top and bottom edges of at least one of the first and second wing members are parallel.

36. The device in accordance with claim 20 wherein each of the first and second lateral interbody wing members has a top edge and a bottom edge; and
wherein at least one edge selected from the group consisting of the top edge of the first wing member, the bottom edge of the first wing member, the top edge of the second wing member and the bottom edge of the second wing member is shaped to reduce subsidence of the edge into an endplate of the first or second vertebra.

37. The device in accordance with claim 20 wherein said plate includes two bone screw receiving apertures in a superior portion of said plate, and two bone screw receiving apertures in an inferior portion of said plate.

38. The device in accordance with claim 20 wherein said plate includes one bone screw receiving aperture in a superior portion of said plate, and one bone screw receiving aperture in an inferior portion of said plate.

39. The device in accordance with claim 20 wherein said plate includes a superior portion defining one bone screw receiving aperture, and an inferior portion defining one bone screw receiving aperture; and
   wherein said superior bone screw receiving aperture and inferior bone screw receiving aperture are offset to the same side of a midline of the vertebrae.

40. The device in accordance with claim 20 wherein said plate includes a superior portion defining one bone screw receiving aperture, and an inferior portion defining one bone screw receiving aperture;
   wherein said superior bone screw receiving aperture is offset to one side of a midline of the vertebrae; and
   wherein said inferior bone screw receiving aperture is offset to the opposite side of the midline.

41. The device in accordance with claim 20 wherein said at least two articular elements comprise:
   a first articular element configured for engagement with the first vertebrae; and
   a second articular element configured for engagement with the second vertebrae.

42. The device in accordance with claim 41 wherein said at least two articular elements together define a joint that permits said first and second articular elements to rotate and pivot relative to one another prior to being at least partially positioned between said interbody wing members.

43. The device in accordance with claim 20 wherein said retention plate has an anterior side, a posterior side, and lateral surfaces extending from said anterior side to said posterior side; and
   wherein said anterior end of each of said first and second wing members is affixed to and extends generally perpendicularly from said posterior side of said retention plate, said first and second wing members having inner surfaces that face toward one another and outer surfaces that face laterally away from one another and which extend from respective ones of said lateral surfaces of said retention plate to thereby provide the disc locking implant device with a U-shaped configuration.

44. The device in accordance with claim 20 wherein said first and second interbody wing members have respective inner surfaces facing generally toward one another; and
   wherein said inner surface of each of said first and second interbody wing members includes lateral contours that engage corresponding lateral contours of said articulating artificial disc to thereby engage said articulating artificial disc to said interbody wing members.

45. The device in accordance with claim 44 wherein said lateral contours defined by said first and second interbody wing members comprise lateral projections; and
   wherein said corresponding lateral contours defined by said articulating artificial disc comprise lateral channels; and
   wherein said lateral projections are positioned within said lateral channels to thereby engage said articulating artificial disc to said disc locking implant.

46. The system in accordance with claim 20 wherein said anterior retention plate has a length adapted to span the interbody space between the first and second vertebrae;
   wherein said anterior retention plate includes a first aperture passing through a superior portion of said plate positioned along a superior side of said artificial disc, said first aperture adapted to receive a first securing element for securing the plate to the first vertebrae; and
   wherein said anterior retention plate includes a second aperture passing through an inferior portion of said plate positioned along an inferior side of said artificial disc, said second aperture adapted to receive a second securing element for securing the plate to the second vertebrae.

* * * * *